US008697620B2

(12) United States Patent
Nishina et al.

(10) Patent No.: US 8,697,620 B2
(45) **Date of Patent: *Apr. 15, 2014**

(54) SOLID SOAP

(71) Applicant: P & PF Co., Ltd., Ibaraki (JP)

(72) Inventors: Tetsuo Nishina, Takatsuki (JP); Takahito Makita, Ibaraki (JP); Tomoko Toda, Sakai (JP); Yoshinobu Saito, Ibaraki (JP); Takahiro Okuda, Machida (JP)

(73) Assignee: P & PF Co., Ltd., Ibaraki-shi, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/745,969

(22) Filed: Jan. 21, 2013

(65) Prior Publication Data

US 2013/0190220 A1 Jul. 25, 2013

(30) Foreign Application Priority Data

Jan. 25, 2012 (JP) ................................ 2012-013044
Feb. 2, 2012 (JP) ................................ 2012-020438

(51) Int. Cl.
*A61K 8/00* (2006.01)

(52) U.S. Cl.
USPC ............ 510/141; 510/152; 510/153; 510/155

(58) Field of Classification Search
None
See application file for complete search history.

(56) References Cited

U.S. PATENT DOCUMENTS

| | | | | |
|---|---|---|---|---|
| 5,264,145 | A | 11/1993 | French et al. | |
| 5,387,362 | A | 2/1995 | Tollens et al. | |
| 2002/0132743 | A1 * | 9/2002 | Saito et al. | 510/141 |
| 2010/0069277 | A1 | 3/2010 | McFann et al. | |

FOREIGN PATENT DOCUMENTS

| | | |
|---|---|---|
| EP | 1219701 | 7/2002 |
| JP | 2001-40390 | 2/2001 |
| WO | 94/09107 | 4/1994 |
| WO | 2004/029190 | 4/2004 |

OTHER PUBLICATIONS

Patent Abstracts of Japan, JP 2001-40390, 9 pages.
European Search Report dated Apr. 12, 2013, five pages.

* cited by examiner

*Primary Examiner* — Necholus Ogden, Jr.
(74) *Attorney, Agent, or Firm* — Rankin, Hill & Clark LLP

(57) ABSTRACT

The object of the present invention is to improve the solidification point and the hardness of a soap of the fatty acid soap series wherein the percentage of potassium used as the counter ion is large. The solid soap of the present invention to achieve the above-described object is characterized by comprising 1 to 5 mass % of a betaine, and in that sodium and potassium are contained as the fatty acid counter ion, and potassium is 20 mole % or more of the counter ion.

6 Claims, No Drawings

SOLID SOAP

RELATED APPLICATIONS

This application claims the priority of Japanese Patent Application No. 2012-013044 filed on Jan. 25, 2012 and Application No. 2012-20438 filed on Feb. 2, 2012, which are incorporated herein by reference.

FIELD OF THE INVENTION

The present invention relates to a solid soap, and in particular, relates to the improvement of a solid soap wherein fatty acid soap is the main component.

BACKGROUND OF THE INVENTION

Common solid soaps are normally produced by a framing method or a milling method by using fatty acid soap as the base and by adding sugars or polyols such as sucrose, glycerin, sorbitol, and propylene glycol as necessary.

The fatty acid counter ion has a large effect on the properties of soap. If sodium is used as the counter ion, the solidification point and the hardness normally increase, and it is easy to adjust the shape as solid soap. On the other hand, the solubility in cold water and the foaming property decrease, and they tend to decrease the cleansing power and the feeling in use. In contrast to this, if potassium is used as the counter ion, the solubility in cold water and the foaming property are largely improved. However, the solidification point and the hardness significantly decrease, and production suitability as solid soap and the shape-retaining property deteriorate. Therefore, potassium is widely used, as the counter ion, for liquid soap (liquid body soap etc.). However, the application of about 20% of potassium has virtually been the limit for solid soap.

Especially in transparent soap, it is necessary to add a substantial amount of sugars or polyols to achieve transparency. Thus, the decrease in the solidification point is large, and the use of potassium as the counter ion tends to be difficult.

That is, the structural mechanism of letting transparent soap be transparent is considered that opaque soap fibrous microcrystals, which are optically discontinuous in size with respect to visible light, are mainly severed perpendicularly to the fiber axes by the addition of the above-described sugars and polyols and refined to the size of a wavelength of visible light or less; as a result, the soap becomes transparent. Therefore, the hardness and the solidification point easily decrease compared with the soap in which sugars and polyols are not added.

In particular, when transparent soap is produced by the framing method without using ethanol as the solvent for sugars and polyols, cutting, shape forming, and packaging are often carried out immediately after the removal of the frame. Thus, the decrease in the solidification point and the decrease in the hardness also directly lead to the deterioration of production suitability.

Therefore, it has been difficult to use potassium, which tends to lower the hardness and solidification point, as the counter ion.

On the other hand, soaps in which amino acids or trimethylglycine is blended are publicly known (Japanese Unexamined Patent Publication No. 2001-40390 and WO2004/029190); however, the presence of adjustment effects for the decrease of the solidification point and the hardness, when a large amount of potassium is used as the counter ion, has been totally unknown.

DISCLOSURE OF THE INVENTION

Problem to be Solved by the Invention

The present invention was made in view of the above-described conventional art, and the problem to be solved is to provide a solid soap in which even when a large amount of potassium is used as the counter ion of fatty acid soap, the solidification point and the hardness can be improved while the properties such as the solubility in cold water and the feeling in use are maintained.

Means to Solve the Problem

In order to achieve the above-described object, the present inventors have investigated the means for increasing the solidification point of fatty acid soap. As a result, the present inventors have discovered that betaines, and in particular, trimethylglycine has an excellent solidification point increasing effect, thus leading to the completion of the present invention.

The solid soap of the present invention to achieve the above-described object is characterized by comprising 1 to 5 mass % of a betaine, and in that sodium and potassium are contained as the fatty acid counter ion, and potassium is 20 mole % or more of the counter ion.

In the above-described solid soap, it is preferable that Na/K=80/20 to 50/50, and 1 to 5 mass % of trimethylglycine is blended as the betaine.

In addition, it is preferable that the above-described solid soap comprises 20 to 70 mass % of fatty acid soap part and 30 to 70 mass % of sugar/polyol part, and it is transparent solid soap in which no ethanol is virtually contained.

Hereinafter, the constitution of the present invention will be described in detail.

[Fatty Acid Soap Part]

The fatty acid in the fatty acid sodium salt or fatty acid sodium/potassium mixed salt used in the soap of the present invention is a saturated or unsaturated fatty acid wherein the number of carbon atoms is preferably 8 to 20 and more preferably 12 to 18, and it may be either linear or branched. Specific examples include lauric acid, myristic acid, palmitic acid, stearic acid, oleic acid, isostearic acid, and mixtures thereof, namely beef tallow fatty acid, coconut oil fatty acid, and palm kernel oil fatty acid.

Specific examples of the fatty acid sodium/potassium mixed salts include sodium/potassium laurate, sodium/potassium myristate, sodium/potassium palmitate, sodium/potassium stearate, sodium/potassium oleate, sodium/potassium isostearate, beef tallow fatty acid sodium/potassium salt, coconut oil fatty acid sodium/potassium salt, and palm kernel oil fatty acid sodium/potassium salt, and these may be used either alone or in combination of two or more. Among the above-described fatty acid sodium/potassium mixed salts, sodium/potassium laurate, sodium/potassium myristate, sodium/potassium palmitate, sodium/potassium stearate, sodium/potassium oleate, and sodium/potassium isostearate can be preferably used.

In the soap of the present invention, the content of fatty acid sodium salt or fatty acid sodium/potassium mixed salt is preferably 20 to 70 mass % in the case of transparent soap. If this content is less than 20 mass %, the transparency decreases or the solidification point decreases. Therefore, when stored for a long period of time, the surface may melt and the commercial value may be lost. On the contrary, if the content exceeds 70 mass %, the transparency may also decrease, and a taut feeling may be generated after use.

In the fatty acid sodium/potassium mixed salt, the mole ratio of sodium and potassium (sodium/potassium ratio), which constitute the salt, is preferably 70/30 to 40/60 and especially preferably 70/30 to 60/40. If this sodium/potassium ratio exceeds 40/60 and the percentage of potassium becomes large, a satisfactory solidification point cannot be obtained even by the addition of a betaine. When stored for a long period of time, the surface may melt and the commercial value may be lost. In addition, the hardness may decrease, the soap reduction through dissolution during use may become large, soap sweating may be caused under the conditions of high temperature and high humidity, and the surface may become cloudy during use.

[Sugar/Polyol Part]

Preferable sugar/polyol examples, when the present invention is used for transparent solid soap, include maltitol, sorbitol, glycerin, 1,3-butylene glycol, propylene glycol, polyethylene glycol, sugar, pyrrolidone carboxylic acid, sodium pyrrolidone carboxylate, hyaluronic acid, and polyoxyethylene alkyl glucoside ether, and it is preferable to blend 30 to 70 mass % thereof in the composition.

In particular, to obtain transparency as well as excellent usability, the ratio of sugars/sugar alcohols and polyols is preferably 40 to 60:60 to 40 in the sugar/polyol part.

[Amphoteric Surfactants]

It is preferable that the solid soap of the present invention contains the following amphoteric surfactant.

As the amphoteric surfactant usable in the solid soap of the present invention, amphoteric surfactants represented by the following chemical formulas (A) to (C) can be listed.

(A)

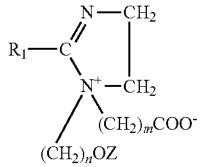

[In the formula, $R_1$ represents an alkyl group or an alkenyl group of 7 to 21 carbon atoms, n and m are the same or different from each other and represent an integer of 1 to 3, and Z represents a hydrogen atom or $(CH_2)_pCOOY$ (here, p is an integer of 1 to 3, and Y is an alkali metal, an alkaline earth metal, or an organic amine).], (B)

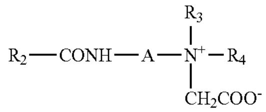

[In the formula, $R_2$ represents an alkyl group or an alkenyl group of 7 to 21 carbon atoms, $R_3$ and $R_4$ are the same or different from each other and represents a lower alkyl group, and A represents a lower alkylene group.], and (C)

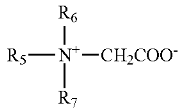

[In the formula, $R_5$ represents an alkyl group or an alkenyl group of 8 to 22 carbon atoms, $R_6$ and $R_7$ are the same or different from each other and represent a lower alkyl group.].

In chemical formula (A), "an alkyl group of 7 to 21 carbon atoms" represented by $R_1$ can be either linear or branched, and the number of carbon atoms is preferably 7 to 17. "An alkenyl group of 7 to 21 carbon atoms" represented by $R_1$ can be either linear or branched, and the number of carbon atoms is preferably 7 to 17. As "an alkali metal" represented by Y, sodium, potassium, etc. can be listed, as "an alkaline earth metal", calcium, magnesium, etc. can be listed, and as "an organic amine", monoethanolamine, diethanolamine, triethanolamine, etc. can be listed.

Specific examples of amphoteric surfactants represented by chemical formula (A) include imidazolinium betaine-type, surfactants such as 2-undecyl-N-carboxymethyl-N-hydroxyethylimidazolium betaine (synthesized from lauric acid; hereinafter, for convenience, also referred to as "lauroyl imidazolinium betaine"), 2-heptadecyl-N-carboxymethyl-N-hydroxyethylimidazolium betaine (synthesized from stearic acid), and 2-alkyl or alkenyl-N-carboxymethyl-N-hydroxyethylimidazolium betaine synthesized from coconut oil fatty acid ($R_1$ is a mixture of $C_7$ to $C_{17}$; hereinafter, for convenience, also referred to as "cocoyl imidazolinium betaine").

In chemical formula (B), "an alkyl group of 7 to 21 carbon atoms" and "an alkenyl group of 7 to 21 carbon atoms" represented by $R_2$ are similar to those represented by $R_1$ of chemical formula (A). "A lower alkyl group" represented by $R_3$ and $R_4$ is linear or branched and preferably an alkyl group of 1 to 3 carbon atoms. "A lower alkylene group" represented by A is linear or branched and preferably an alkylene group of 3 to 5 carbon atoms.

Specific examples of amphoteric surfactants represented by chemical formula (B) (amidoalkyl betaine-type) include amidopropyl betaine-type surfactants such as coconut oil fatty acid amidopropyldimethylaminoacetic acid betaine ($R_2$ is a mixture of $C_7$ to $C_{17}$).

In chemical formula (C), "an alkyl group of 8 to 22 carbon atoms" represented by $R_5$ can be either linear or branched, and the number of carbon atoms is preferably 8 to 18. "An alkenyl group of 8 to 22 carbon atoms" represented by $R_5$ can be either linear or branched, and the number of carbon atoms is preferably 8 to 18. "A lower alkyl group" represented by $R_6$ and $R_7$ is similar to the one represented by $R_3$ and $R_4$ of chemical formula (B).

Specific examples of amphoteric surfactants (alkyl betaine-type) represented by chemical formula (C) include lauryldimethylaminoacetic acid betaine and alkyl or alkenyldimethylaminoacetic acid betaine ($R_5$ is a mixture $C_8$ to $C_{18}$) synthesized from coconut oil fatty acid.

In the present invention, at least one surfactant is selected for use from the group consisting of amphoteric surfactants represented by the above-described chemical formulas (A) to (C).

In the solid soap of the present invention, when the above-described amphoteric surfactant is blended, the fatty acid soap (fatty acid sodium salt or fatty acid sodium/potassium mixed salt) and the amphoteric surfactant form a composite salt. Thus, the usability such as "a coarse feeling" is improved and the hardness is also improved; as a result, the effect such as the lowering of soap reduction through dissolution can be achieved.

In the solid soap of the present invention, the content of the above-described amphoteric surfactant is preferably 1 to 15 mass %, and especially preferably 4 to 8 mass %. If this content is less than 1 mass %, the solidification point becomes low. Thus, when stored for a long period of time, the surface may melt and the commercial value may be lost. In addition, the hardness may decrease, and the soap reduction through dissolution during use may become large. In addition, the transparency may decrease. On the contrary, if the content exceeds 15 mass %, a sticky feeling is generated after use. In addition, when stored for a long period of time, the surface changes to brown and the commercial value may be lost.

[Nonionic Surfactants]

It is preferable to further blend a nonionic surfactant to the solid soap of the present invention. Examples of usable nonionic surfactants include polyoxyethylene (hereinafter also referred to as "POE") hydrogenated castor oil, polyoxyethylene 2-octyldodecyl ether, polyoxyethylene lauryl ether, propylene oxide/ethylene oxide block copolymer, polyoxyethylene polyoxypropylene cetyl ether, polyoxyethylene polyoxypropylene glycol, polyethylene glycol diisostearate, alkyl glucoside, polyoxyethylene-modified silicone (for example, polyoxyethylene alkyl-modified dimethylsilicone), polyoxyethylene-glycerin monostearate, and polyoxyethylene alkyl glucoside. These may be used either alone or in combination of two or more. Among the above-described nonionic surfactants, polyoxyethylene hydrogenated castor oil and propylene oxide/ethylene oxide block copolymer are preferably used.

In the solid soap of the present invention, a more usability improving effect can be achieved by blending a nonionic surfactant.

The content of a nonionic surfactant in the solid soap of the present invention is preferably 1 to 15 mass %, and especially preferably 6 to 12 mass %. If this content is less than 1 mass %, a taut feeling may be generated after use. On the contrary, if the content exceeds 15 mass %, the solidification point decreases. Thus, when stored for a long period of time, the surface may melt and the commercial value may be lost. In addition, the hardness may decrease, and the soap reduction through dissolution during use may become large. In addition, a sticky feeling may be generated after use.

[Hydroxyalkyl Ether Carboxylic Acid Salt-Type Surfactants]

It is preferable to add a hydroxyalkyl ether carboxylic acid salt-type surfactant to the solid soap of the present invention; then the improvement in foaming can be observed.

The preferable hydroxyalkyl ether carboxylic acid salt-type surfactant, in the present invention, has the following structure (D).

(D)

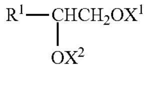

(In the formula, $R^1$ represents a saturated or unsaturated hydrocarbon group of 4 to 34 carbon atoms; either one of $X^1$ and $X^2$ represents $—CH_2COOM^1$, and the other one represents a hydrogen atom; and $M^1$ represents a hydrogen atom, an alkali metal, an alkaline earth metal, ammonium, a lower alkanol amine cation, a lower alkyl-amine cation, or a basic amino acid cation.)

In the formula, $R^1$ is either an aromatic hydrocarbon or a linear or branched aliphatic hydrocarbon; however, an aliphatic hydrocarbon, especially an alkyl group or an alkenyl group is preferable. Preferable examples include a butyl group, an octyl group, a decyl group, a dodecyl group, a tetradecyl group, a hexadecyl group, an octadecyl group, a docosyl group, a 2-ethylhexyl group, a 2-hexyldecyl group, a 2-octylundecyl group, a 2-decyltetradecyl group, a 2-undecylhexadecyl group, a decenyl group, a dodecenyl group, a tetradecenyl group, and a hexadecenyl group. Among them, a decyl group and a dodecyl group have advantage in the surface-active power.

In the formula, either one of $X^1$ and $X^2$ is represented by $—CH_2COOM^1$, and the examples of $M^1$ include a hydrogen atom, lithium, potassium, sodium, calcium, magnesium, ammonium, monoethanolamine, diethanolamine, and triethanolamine.

Specifically, among the above-described (A) hydroxyalkyl ether carboxylic acid salt-type surfactants, sodium dodecane-1,2-diol acetate ether, in which H of either of the OH groups of dodecane-1,2-diol is replaced with $—CH_2COONa$, is most preferable in the present invention.

In the present invention, 1 to 15 mass % and preferably 5 to 10 mass % of hydroxyalkyl ether carboxylic acid salt-type surfactant can be blended from the viewpoint of foaming improvement.

In the present invention, the following components can be optionally blended as additives other than the above-described components so far as the above-described effect is not impaired. These optional components are disinfectants such as trichlorocarbanilide and hinokitiol; oil; perfume; pigment; chelating agents such as trisodium edetate dihydrate; UV absorbers; antioxidants; natural extracts such as dipotassium glycyrrhizinate, plantago herb extract, lecithin, saponin, aloe, phellodendron bark, and chamomile; nonionic, cationic or anionic water-soluble polymers; usability improvers such as lactic acid esters, etc.

When a chelating agent is used in the cleansing composition of the present invention, hydroxyethane diphosphonic acid and salts thereof are preferable examples, and the more preferable example is hydroxyethane diphosphonic acid. The blending quantity is preferably 0.001 to 1.0 mass %, and more preferably 0.1 to 0.5 mass %. If the blending quantity of hydroxyethane diphosphonic acid and salts thereof is less than 0.001 mass %, the chelate effect is insufficient, and unfavorable yellow discoloration etc. takes place with time. If the blending quantity is more than 1.0 mass %, the irritation to the skin becomes strong and it is not desirable.

As the production method of the soap of the present invention, general methods such as the framing method and the milling method can be applied to the above-described mixture of each component.

When transparent soap is made as the solid soap of the present invention, the soap with decreased transparency because of blended pigment etc. is also included.

Effect of the Invention

As explained above, in the soap of the present invention, the use of 20 mole % or more of potassium, as the counter ion of fatty acid soap, becomes possible by the addition of a betaine. Thus, adequate formability and shape-retaining property can be achieved while the solubility in cold water and the foaming property are maintained.

BEST MODE FOR CARRYING OUT THE INVENTION

Hereinafter, the best modes for carrying out the present invention will be described.

The present inventors have carried out the investigation by using the following basic formulation to improve the foaming property of transparent soap of the fatty acid soap series. The blending quantities are shown in mass %.

First, the present inventors attempted the production of transparent solid soap by using the soap of the basic formulation consisting of the below-described soap part, sugar/polyol part, and others.

Basic Formulation

| | |
|---|---|
| Fatty acid soap part | 30.0% |
| Lauric acid | 28 parts |
| Myristic acid | 52 parts |
| Stearic acid | 15 parts |
| Isostearic acid | 5 parts |

Neutralized with sodium hydroxide:potassium hydroxide (mole ratio) listed in each table

| | |
|---|---|
| Sugar/polyol part | 40.0% |
| 1,3-BG | 15.0 parts |
| PEG1500 | 2.5 parts |
| Sorbitol | 20.0 parts |
| Sucrose | 23.0 parts |
| Glycerin | 30.0 parts |
| Others | 30.0% |
| Trimethylglycine | X % |
| Sodium dodecane-1,2-diol acetate ether | 1.0% |
| Sodium N-lauroyl-N'-carboxymethyl-N'-hydroxyethylethylenediamine | 2.0% |
| PEG-60 hydrogenated castor oil | 5.0% |
| Chelating agent | 0.1% |
| Ion-exchanged water | balance |

In the following test, the foaming power was measured by mixer method with a foaming machine. That is, 1% aqueous soap solution (artificial hard water: 70 ppm, temperature: 25° C.) was prepared, and the height of foam after stirring for 20 seconds was measured.

The solubility by rubbing was measured according to JISK-3304. That is, a test specimen (cross section: 15 mm×20 mm) with a fixed weight was placed on the surface of a film wetted by tap water that had been adjusted to 40° C. and dissolved by rubbing for 10 minutes by rotating the film. From the weights before and after dissolution by rubbing, the solubility by rubbing per fixed area was determined by the following equation.

$$\text{Solubility by rubbing} = (\text{weight before} - \text{weight after}) \times 100/3.$$

The hardness was shown by the maximum stress, when a needle was pressed into a depth of 10 mm from the soap surface, measured with a rheometer (manufactured by Fudoh Kogyo Co.).

Other evaluations were by the usual methods.

The comprehensive evaluation was carried out based mainly on the solidification point and the hardness.

For the solidification point: X (40° C. or lower), Δ (40 to 45° C.), ○ (45 to 50° C.), and ◎ (50° C. or higher).

For the hardness: X (400 or lower), Δ (400 to 450), ○ (450 to 500), and ◎ (500 or higher).

For other evaluation items, the evaluation was also taken into consideration when they were poor.

First, the present inventors fixed the percentages of the fatty acid soap part, sugar/polyol part, and others of the above-described basic formulation. Then, the fraction of counter ions was sequentially changed, and the verification of the addition effect of trimethylglycine was carried out.

The results are shown in Tables 1 to 5.

TABLE 1

| Na/K = 80/20 | | | | | |
|---|---|---|---|---|---|
| | Test Example | | | | |
| | 1-1 | 1-2 | 1-3 | 1-4 | 1-5 |
| Trimethylglycine (%) | 0 | 1 | 2 | 3 | 4 |
| Solidification point | 50.7 | 52.8 | 55.5 | 56.5 | 59.4 |
| Appearance | ○ | ○ | ○ | Δ | X |
| Hardness | 457 | 517 | 577 | 593 | 613 |
| Solubility by rubbing (25° C.) | 19 | 21 | 17 | 16 | 20 |
| Solubility by rubbing (40° C.) | 62 | 69 | 59 | 60 | 66 |
| Formability (25° C.) | 2100 | 2100 | 2100 | 2000 | 2100 |
| Formability (40° C.) | 2350 | 2300 | 2300 | 2300 | 2300 |
| Comprehensive evaluation | Δ | Δ | Δ | X | X |

The above Table 1 shows composition examples for Na/K=80/20. Without blending trimethylglycine, both the solidification point and the hardness were in the problem-free range (Test Example 1-1). However, the foam property and the solubility by rubbing had some drawbacks. By blending trimethylglycine, the solidification point and the hardness increased, and the improvement of the foam property was observed. However, crystals were generated, and the appearance as transparent soap deteriorated though basic soap functions were not affected.

Table 2

| Na/K = 70/30 | | | | | | | |
|---|---|---|---|---|---|---|---|
| | Test Example | | | | | | |
| | 2-1 | 2-2 | 2-3 | 2-4 | 2-5 | 2-6 | 2-7 |
| Trimethylglycine (%) | 0 | 1 | 2 | 3 | 4 | 5 | 6 |
| Solidification point | 49.2 | 50.5 | 51.5 | 54.4 | 56.5 | 59.1 | 55.4 |
| Appearance | ○ | ○ | ○ | ○ | Δ | X | X |
| Hardness | 427 | 483 | 503 | 593 | 700 | 760 | 673 |
| Solubility by rubbing (25° C.) | 22 | 21 | 21 | 20 | 22 | 19 | 21 |
| Solubility by rubbing (40° C.) | 66 | 67 | 68 | 69 | 68 | 66 | 74 |
| Formability (25° C.) | 2300 | 2200 | 2200 | 2100 | 2200 | 2200 | 2200 |
| Formability (40° C.) | 2300 | 2250 | 2400 | 2300 | 2400 | 2400 | 2350 |
| Comprehensive evaluation | Δ | ○ | ◎ | ◎ | Δ | X | X |

The above Table 2 shows composition examples for Na/K=70/30. In Test Example 2-1, wherein trimethylglycine was not blended, both the solidification point and the hardness became lower than those of Test Example 1-1 (Na/K=80/20), and approached the lower limit for practical use. On the other hand, it can be understood that the solubility by rubbing at a low temperature and the foaming property at a low temperature increase and the usability at a low temperature increases.

As shown in Test Examples 2-2 to 2-4, the solidification point and the hardness can be increased by adding 1 to 2% of trimethylglycine while maintaining the solubility by rubbing and the foaming power. In addition, even when trimethylglycine is increased to 4 to 5%, the function of soap itself is not hindered in particular. However, the aesthetic appearance as transparent soap is affected with crystallization.

Table 3

| Na/K = 60/40 | Test Example | | | | | | |
|---|---|---|---|---|---|---|---|
| | 3-1 | 3-2 | 3-3 | 3-4 | 3-5 | 3-6 | 3-7 |
| Trimethylglycine (%) | 0 | 1 | 2 | 3 | 4 | 5 | 6 |
| Solidification point | 44.7 | 48.3 | 48.4 | 50.6 | 52.8 | 54.8 | 52.4 |
| Appearance | ○ | ○ | ○ | ○ | ○ | ○ | Δ |
| Hardness | 370 | 389 | 413 | 460 | 473 | 527 | 587 |
| Solubility by rubbing (25° C.) | 23 | 23 | 29 | 26 | 26 | 25 | 27 |
| Solubility by rubbing (40° C.) | 74 | 71 | 69 | 71 | 71 | 68 | 73 |
| Formability (25° C.) | 2300 | 2200 | 2200 | 2250 | 2150 | 2200 | 2200 |
| Formability (40° C.) | 2400 | 2300 | 2250 | 2350 | 2350 | 2300 | 2350 |
| Comprehensive evaluation | X | X | Δ | ○ | ○ | ◎ | Δ |

The above Table 3 shows composition examples for Na/K=60/40. In Test Example 3-1, wherein trimethylglycine was not blended, the solidification point was lower than 45° C. and the hardness was lower than 400. Therefore, problems can be generated in the production operation, in which molten soap is solidified by cooling in the cooling frame, and also during use.

On the other hand, Test Examples 3-2 to 3-5, wherein 1 to 4% of trimethylglycine was blended, the solidification point and the hardness could be increased without the deterioration of the solubility by rubbing and the foaming property. However, when the blending quantity of trimethylglycine was 6%, crystallization took place as expected. Although the basic function of the soap was not affected, the transparency as transparent soap had a declining trend.

Table 4

| Na/K = 50/50 | Test Example | | | | | | |
|---|---|---|---|---|---|---|---|
| | 4-1 | 4-2 | 4-3 | 4-4 | 4-5 | 4-6 | 4-7 |
| Trimethylglycine (%) | 0 | 1 | 2 | 3 | 4 | 5 | 6 |
| Solidification point | 40.1 | 42.8 | 43.0 | 46.4 | 48.6 | 49.6 | 49.8 |
| Appearance | ○ | ○ | ○ | ○ | ○ | ○ | Δ |
| Hardness | 263 | 273 | 293 | 337 | 360 | 397 | 417 |
| Solubility by rubbing (25° C.) | 28 | 26 | 26 | 29 | 30 | 31 | 32 |
| Solubility by rubbing (40° C.) | 79 | 83 | 80 | 78 | 79 | 78 | 78 |
| Formability (25° C.) | 2200 | 2250 | 2150 | 2200 | 2250 | 2200 | 2300 |
| Formability (40° C.) | 2400 | 2300 | 2300 | 2300 | 2350 | 2350 | 2300 |
| Comprehensive evaluation | X | X | X | X | Δ | Δ | Δ |

The above Table 4 shows composition examples for Na/K 50/50; they showed a nearly similar trend to the cases of Na/K=60/40 shown in the above Table 3. Test Examples 4-5 and 4-6 showed low hardness; however, there was no issue in production suitability and evaluated to be Δ.

TABLE 5

| Na/K = 40/60 | Test Example | |
|---|---|---|
| | 5-1 | 5-2 |
| Trimethylglycine (%) | 7 | 8 |
| Solidification point | 48.3 | 49.2 |
| Appearance | ○ | Δ |
| Hardness | 290 | 343 |
| Solubility by rubbing (25° C.) | 32 | 32 |
| Solubility by rubbing (40° C.) | 83 | 85 |
| Formability (25° C.) | 2150 | 2150 |
| Formability (40° C.) | 2300 | 2350 |
| Comprehensive evaluation | X | Δ |

The above Table 5 shows composition examples of Na/K=40/60. As shown in Test Example 5-2, the hardness was low because of the blending of about 8% of trimethylglycine. However, the production suitability was in the acceptable range, but the transparency decreased.

As described above, the addition effect of trimethylglycine, which is characteristic of the present invention, was observed in the ranges of Na/K=80/20 to 50/50 and 1 to 8% of trimethylglycine, and it was especially notable in the ranges of Na/K=70/30 to 50/50 and 1 to 5 mass % of trimethylglycine.

Transparent solid soap shown in the above Tables 1 to 5 was produced without virtually using ethyl alcohol at the time of production. They are the so-called alcohol-free-type, and the merit of the addition of trimethylglycine is especially large.

That is, when the so-called alcohol-type transparent solid soap is produced by the framing method in which 10 to 20% or more of ethyl alcohol is used at the time of production, molten soap is poured into a long cylindrical cooling frame, cooled, and cut after the removal of the soap material bar from the cooling frame. Then, aging is carried out over a long period of time (several days to several weeks) to remove the ethyl alcohol used at the time of production. So far as such an alcohol-type framed soap has hardness to the degree that the removal of the soap material bar from the cooling frame is possible and the cutting is possible, an increase in the hardness is observed during the subsequent aging period, and shape forming becomes possible, as necessary, after aging.

However, in the case of the above-described alcohol-free-type, there is a merit in that aging is not necessary because no ethyl alcohol is virtually used (5% or less at the most). On the other hand, the removal of the soap material bar, cutting, and shape forming are continuously carried out. Thus, the shortening of cooling time (increase in the solidification point) and the hardness (cutting, formability) are very important.

In this point, the addition effect (increase in the solidification point, increase in the hardness) of trimethylglycine, in the present invention, is especially useful.

Furthermore, the present inventors have carried out the verification of the effect for glycine, which is a related substance to trimethylglycine. The results are shown in Table 6.

TABLE 6

Na/K = 80/20

| | Test Example | | |
|---|---|---|---|
| | 6-1 | 6-2 | 6-3 |
| Glycine (%) | 1 | 3 | 5 |
| Solidification point | 53.9 | 51.7 | 47.7 |
| Appearance | Δ | X | X |
| Hardness | 687 | 680 | 680 |
| Solubility by rubbing (25° C.) | 13 | 8 | 2 |
| Solubility by rubbing (40° C.) | 57 | 55 | 42 |
| Formability (25° C.) | 2100 | 2050 | 1100 |
| Formability (40° C.) | 2350 | 2150 | 1400 |
| Comprehensive evaluation | Δ | X | X |

For glycine, a hardening effect was somewhat observed at a low concentration; however, there was a case in that the color of appearance turned yellow, and a strange smell also was generated during storage.

Thus, it is understood that the soap property improving effect by trimethylglycine is a unique effect that cannot be seen for other amino acids.

What is claimed is:

1. A solid soap comprising:

1 to 5 mass % of trimethylglycine, wherein sodium and potassium are contained as a fatty acid counter ion, and wherein potassium is 20 mole % or more of the counter ion.

2. The solid soap according to claim 1, wherein a mole ratio of sodium/potassium is from 80/20 to 50/50.

3. The solid soap according to claim 1, comprising:

20 to 70 mass % of a fatty acid soap part, and 30 to 70 mass % of a sugar and polyol part, wherein no ethanol is contained.

4. The solid soap according to claim 3, wherein the solid soap is transparent.

5. The solid soap according to claim 2, comprising:

20 to 70 mass % of a fatty acid soap part, and 30 to 70 mass % of a sugar and polyol part, wherein no ethanol is contained.

6. The solid soap according to claim 5, wherein the solid soap is transparent.

* * * * *